(12) United States Patent
Beier et al.

(10) Patent No.: US 8,796,463 B2
(45) Date of Patent: Aug. 5, 2014

(54) FUNGICIDE HYDROXIMOYL-TETRAZOLE DERIVATIVES

(75) Inventors: Christian Beier, Bergisch Gladbach (DE); Jurgen Benting, Leichlingen (DE); David Bernier, Lyons (FR); Pierre-Yves Coqueron, Lyons (FR); Philippe Desbordes, Lyons (FR); Christophe Dubost, Charbonnieres-les-Bains (FR); Stephanie Gary, Champagne-au-Mont-d'Or (FR); Pierre Genix, Lyons (FR); Daniela Portz, Vettweiss (DE); Ulrike Wachendorff-Neumann, Neuwied (DE)

(73) Assignee: Bayer Cropscience AG (DE)

( * ) Notice: Subject to any disclaimer, the term of this patent is extended or adjusted under 35 U.S.C. 154(b) by 7 days.

(21) Appl. No.: 13/519,293

(22) PCT Filed: Dec. 28, 2010

(86) PCT No.: PCT/EP2010/070773
§ 371 (c)(1),
(2), (4) Date: Sep. 20, 2012

(87) PCT Pub. No.: WO2011/080256
PCT Pub. Date: Jul. 7, 2011

(65) Prior Publication Data
US 2013/0123305 A1   May 16, 2013

(30) Foreign Application Priority Data
Dec. 28, 2009   (EP) .................................... 09356070

(51) Int. Cl.
*C07D 277/00*   (2006.01)
*C07D 401/00*   (2006.01)

(52) U.S. Cl.
USPC ...................................... 548/195; 546/268.4

(58) Field of Classification Search
USPC ...................................... 548/195; 546/268.4
See application file for complete search history.

(56) References Cited

U.S. PATENT DOCUMENTS

| 7,183,299 B2 * | 2/2007 | Kobori et al. ................. 514/361 |
| 2005/0070439 A1 | 3/2005 | Kobori et al. ................. 504/261 |
| 2007/0105926 A1 | 5/2007 | Kobori et al. ................. 514/381 |
| 2010/0286173 A1 | 11/2010 | Beier et al. ..................... 514/256 |

FOREIGN PATENT DOCUMENTS

| EP | 1 426 371 A1 | 6/2004 |
| JP | 2004-131392 | 4/2004 |
| WO | WO 2009/090237 A2 | 7/2009 |
| WO | WO 2011/080254 | 7/2011 |
| WO | WO 2011/080255 | 7/2011 |

OTHER PUBLICATIONS

U.S. Appl. No. 13/516,675, corresponding to PCT/EP2010/070771, having an International filing date of Dec. 28, 2010, published as WO 2011/080254 by Christian Beier et al., entitled Fungicide Hydroximoyl-Tetrazole Derivatives.
U.S. Appl. No. 13/518,753, corresponding to PCT/EP2010/070772, having an International filing date of Dec. 28, 2010, published as WO 2011/080255 by Christian Beier et al., entitled Fungicidal Hydroximoyl-Tetrazole Derivatives.
International Search Report issued Mar. 16, 2011 in corresponding International Application No. PCT/EP2010/070773.

* cited by examiner

*Primary Examiner* — Nizal Chandrakumar
(74) *Attorney, Agent, or Firm* — Ostrolenk Faber LLP

(57) ABSTRACT

The present invention relates to hydroximoyl-tetrazole derivatives of formula (I), their process of preparation, their use as fungicide active agents, particularly in the form of fungicide compositions and methods for the control of phytopathogenic fungi, notably of plants, using these compounds or compositions.

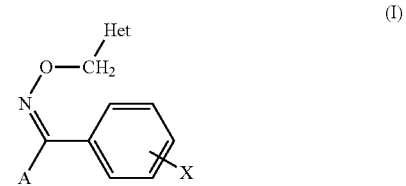

wherein A represents a tetrazoyl group, Het represents a pyridyl group or a thiazolyl group and X represents various substituents.

17 Claims, No Drawings

FUNGICIDE HYDROXIMOYL-TETRAZOLE DERIVATIVES

CROSS-REFERENCE TO RELATED APPLICATION(S)

The present application is a 35 U.S.C. §371 national phase conversion of PCT/EP2010/070773 filed Dec. 28, 2010, which claims priority of European Application No. 09356070.4 filed Dec. 28, 2009. Applicants claim priority to each of the foregoing patent applications. The PCT International Application was published in the English language.

The present invention relates to hydroximoyl-tetrazole derivatives, their process of preparation, their use as fungicide active agents, particularly in the form of fungicide compositions and methods for the control of phytopathogenic fungi, notably of plants, using these compounds or compositions.

In European patent application no 1426371, there are disclosed certain tetrazoyloxime derivatives of the following chemical structure:

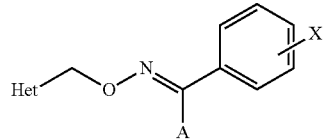

wherein A represents a tetrazolyl group, Het represents either a particular pyridinyl group or a particular thiazolyl group.

In Japanese patent application no 2004-131392, there are disclosed certain tetrazoyloxime derivatives of the following chemical structure:

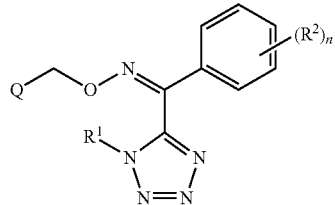

wherein Q can be selected in a list of 15 various heterocycle groups.

In world patent application no 2009-130900, there are disclosed certain tetrazoyloxime derivatives of the following chemical structure:

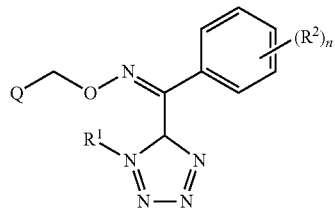

wherein Q can be selected among a pyridinyl group or a thiazolyl group.

The compounds disclosed in these three documents do not prove to provide a comparable utility than the compounds according to the invention.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides a tetrazoyloxime derivative of formula (I)

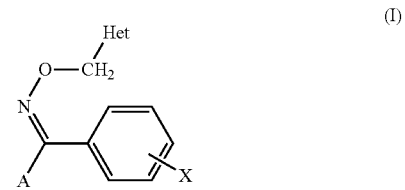

wherein
X represents a hydrogen atom, a halogen atom, substituted or non-substituted $C_1$-$C_8$-alkyl, a substituted or non-substituted $C_1$-$C_8$-alkoxy, a cyano group, a methanesulfonyl group, a nitro group, a trifluoromethyl group or an aryl group;
A represents a tetrazoyl group of formula ($A^1$) or ($A^2$):

wherein Y represents substituted or non-substituted $C_1$-$C_8$-alkyl; and
Het represents a pyridyl group of formula ($Het^1$) or a thiazolyl group of formula ($Het^2$);

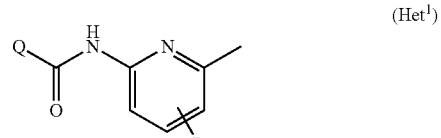

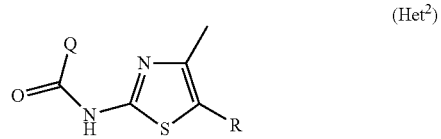

wherein
R represents a hydrogen atom or a halogen atom and
Q represents a group of formula Z;

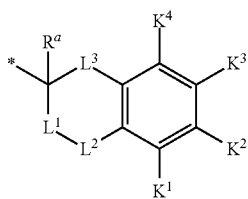

(Z)

wherein
  $R^a$ represents a hydrogen atom, a halogen atom or substituted or non-substituted $C_1$-$C_8$-alkyl,
  $L^1$ represents a divalent group of formula —$(CR^1R^2)_n$—
    wherein
    n represents 1 or 2;
    $R^1$ and $R^2$ independently represent a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted substituted or non-substituted $C_2$-$C_8$-$C_2$-$C_8$-alkenyloxy, halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms;
  $L^2$ represents an oxygen atom, a sulphur atom, a divalent group of formula —$CH_2$— or a carbonyl group;
  $L^3$ represents an oxygen atom or a sulphur atom;
  $K^1$, $K^2$, $K^3$ and $K^4$ independently represent a hydrogen atom, a halogen atom, a nitro group, a hydroxy group, a cyano group, an isonitrile group, an amino group, a sulphanyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphanyl group, a formylamino group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphanyl, substituted or non-substituted $C_1$-$C_8$-halogenoalkylsulphanyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted $C_1$-$C_8$-alkylcarbamoyl, substituted or non-substituted di-$C_1$-$C_8$-alkylcarbamoyl, substituted or non-substituted $C_1$-$C_8$-alkoxycarbonyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_8$-alkynyloxyimino)-$C_1$-$C_8$-alkyl, substituted or non-substituted (benzyloxyimino)-$C_1$-$C_8$-alkyl, substituted or non-substituted benzyloxy, substituted or non-substituted benzylsulphanyl, substituted or non-substituted benzylamino, substituted or non-substituted phenoxy, substituted or non-substituted phenylsulphanyl, substituted or non-substituted phenylamino, substituted or non-substituted aryl, substituted or non-substituted heterocyclyl, substituted or non-substituted tri($C_1$-$C_8$-alkyl)silyloxy, substituted or non-substituted tri ($C_1$-$C_8$-alkyl)silyl, substituted or non-substituted $C_5$-$C_{12}$-fused bicycloalkyl, or substituted or non-substituted $C_5$-$C_{12}$-fused bicycloalkenyl;
or
Q represents a group of formula Z1;

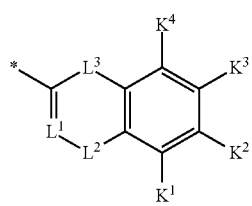

($Z^1$)

wherein
  $L^1$ represents a divalent group of formula =$(CR^1)$— and wherein $R^1$, $K^1$, $K^2$, $K^3$, $K^4$; $L^2$ and $L^3$ have the values described for (Z), or
Q represents a group of formula $Z^2$;

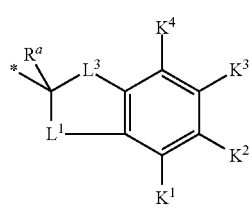

($Z^2$)

wherein $K^1$, $K^2$, $K^3$, $K^4$, $R^a$, $L^1$ and $L^3$ have the values described for (Z);
or
Q represents also a group of formula $Z^3$;

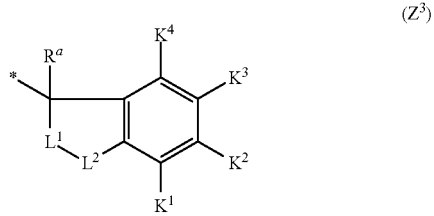

wherein $K^1$, $K^2$, $K^3$, $K^4$, $R^a$, $L^1$ and $L^2$ have the values described for (Z).

as well as salts, N-oxides, metallic complexes and metalloidic complexes thereof or (E) and (Z) isomers and mixtures thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

Notably, the stereostructure of the oxime moiety present in the heterocyclyloxime derivative of formula (I) includes (E) or (Z) isomer, and these stereoisomers form part of the present invention.

According to the invention, the following generic terms are generally used with the following meanings:

halogen means fluorine, chlorine, bromine or iodine;
heteroatom can be nitrogen, oxygen or sulphur;
unless indicated otherwise, a group or a substituent that is substituted according to the invention can be substituted by one or more of the following groups or atoms: a halogen atom, a nitro group, a hydroxy group, a cyano group, an isocyano group, an amino group, a sulphenyl group, a pentafluoro-$\lambda^6$-sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a formylamino group, a (hydroxyimino)-$C_1$-$C_6$-alkyl group, a $C_1$-$C_8$-alkyl, a tri($C_1$-$C_8$-alkyl)silyl-$C_1$-$C_8$-alkyl, $C_1$-$C_8$-cycloalkyl, tri($C_1$-$C_8$-alkyl)silyl-$C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulphenyl, a $C_1$-$C_8$-halogenoalkylsulphenyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkyl-sulphonyl, a $C_1$-$C_8$-halogenoalkylsulphonyl having 1 to 5 halogen atoms, a $C_1$-$C_8$-alkylaminosulfamoyl, a di-$C_1$-$C_8$-alkylaminosulfamoyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, benzyloxy, benzylsulphenyl, benzylamino, phenoxy, phenylsulphenyl, or phenylamino;

the term "aryl" means phenyl or naphthyl;
the term "heterocyclyl" means saturated or unsaturated 4-, 5-, 6-, 7-, 8-, 9-, or 10-membered ring comprising up to 4 heteroatoms selected in the list consisting of N, O, S.

Preferred compounds of formula (I) according to the invention are those wherein the substitution position of X is not specifically limited.

Other preferred compounds of formula (I) according to the invention are those wherein X represents a hydrogen atom, a halogen atom, substituted or non-substituted $C_1$-$C_8$-alkyl, a substituted or non-substituted $C_1$-$C_8$-alkoxy, a cyano group, a methanesulfonyl group, a nitro group, a trifluoromethyl group or an aryl group.

Examples of a halogen atom for X include a chlorine atom, a bromine atom, an iodine atom, and a fluorine atom. Among these halogen atoms, a chlorine atom or a fluorine atom is particularly preferred. The substituted or non-substituted $C_1$-$C_8$-alkyl group represented for X is preferably an alkyl group having 1 to 4 carbon atoms and specific examples thereof include a methyl group, an ethyl group, an n-propyl group, an isopropyl group, an n-butyl group, an isobutyl group, a sec-butyl group, and a tert-butyl group. Among these alkyl groups, a methyl group or a tert-butyl group is particularly preferred. The alkoxy group for X is preferably a substituted or non-substituted $C_1$-$C_8$-alkoxy group having 1 to 3 carbon atoms and specific examples thereof include a methoxy group, an ethoxy group, a propoxy group, and an isopropoxy group. Among these alkoxy groups, a methoxy group or an ethoxy group is particularly preferred.

Even more preferred compounds of formula (I) according to the invention are those wherein X represents a hydrogen atom.

Other preferred compounds of formula (I) according to the invention are those wherein Y represents a substituted or non-substituted $C_1$-$C_8$-alkyl group. Among these alkyl groups, an alkyl group having 1 to 3 carbon atoms such as a methyl group, an ethyl group, an n-propyl group or an isopropyl group is preferable. Among these alkyl groups, a methyl group or an ethyl group is particularly preferred.

Other preferred compounds of formula (I) according to the invention are those wherein R in the pyridyl group of formula (Het$^1$) represents a hydrogen atom or a halogen atom such as a chlorine atom, a bromine atom, an iodine atom or a fluorine atom. Among these, a hydrogen atom or a chlorine atom is particularly preferred.

Other preferred compounds of formula (I) according to the invention are those wherein $R^a$ in the group of formula Q represents a hydrogen atom, a fluorine atom or a methyl group.

Other preferred compounds of formula (I) according to the invention are those wherein n in the group of formula Q represents 1.

Other preferred compounds of formula (I) according to the invention are those wherein $R^1$ and $R^2$ in the group of formula Q independently represent a hydrogen atom, a halogen atom, substituted or non-substituted $C_1$-$C_8$-alkyl.

Other more preferred compounds of formula (I) according to the invention are those wherein $R^1$ and $R^2$ in the group of formula Q independently represent a hydrogen atom, a fluorine atom, or a methyl group.

Other preferred compounds of formula (I) according to the invention are those wherein $L^2$ in the group of formula Q represents an oxygen atom or a divalent group of formula —$CH_2$.

Other preferred compounds of formula (I) according to the invention are those wherein $L^3$ in the group of formula Q represents an oxygen atom.

Other preferred compounds of formula (I) according to the invention are those wherein $K^1$, $K^2$, $K^3$ and $K^4$ in the group of formula Q independently represent a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_3$-$C_8$-alkynyloxy, substituted or non-substituted ($C_1$-$C_6$-alkoxyimino)-$C_1$-$C_6$-alkyl, substituted or non-substituted phenoxy, substituted or non-substituted aryl, substituted or non-substituted heterocyclyl.

Other more preferred compounds of formula (I) according to the invention are those wherein $K^1$, $K^2$, $K^3$ and $K^4$ in the group of formula Q independently represent a hydrogen atom, a halogen atom, a cyano group, substituted or non-substituted $C_1$-$C_8$-alkyl, substituted or non-substituted $C_1$-$C_8$-halogenoalkyl having 1 to 5 halogen atoms, substituted or non-substituted $C_1$-$C_8$-alkoxy.

Other even more preferred compounds of formula (I) according to the invention are those wherein $K^1$, $K^2$, $K^3$ and $K^4$ in the group of formula Q independently represent a hydrogen atom, a halogen atom, a cyano group, $C_1$-$C_2$-alkyl, $C_1$-$C_2$-halogenoalkyl having 1 to 5 halogen atoms, $C_1$-$C_2$-alkoxy.

The above mentioned preferences with regard to the substituents of the compounds of formula (I) according to the invention can be combined in various manners. These combinations of preferred features thus provide sub-classes of compounds according to the invention. Examples of such sub-classes of preferred compounds according to the invention can combine:

preferred features of X with preferred features of one or more of $A^1$, $A^2$, Y, $Het^1$, $Het^2$, R and Q;
preferred features of $A^1$ with preferred features of one or more of X, $A^2$, Y, $Het^1$, $Het^2$, R and Q;
preferred features of $A^2$ with preferred features of one or more of X, $A^1$, Y, $Het^1$, $Het^2$, R and Q;
preferred features of Y with preferred features of one or more of X, $A^2$, $A^1$, $Het^1$, $Het^2$, R and Q
preferred features of $Het^1$ with preferred features of one or more of X, $A^1$, $A^2$, Y, $Het^2$, R and Q
preferred features of R with preferred features of one or more of X, $A^1$, $A^2$, Y, $Het^1$, $Het^2$ and Q;
preferred features of Q with preferred features of one or more of X, $A^1$, $A^2$, Y, $Het^1$, $Het^2$ and R.

In these combinations of preferred features of the substituents of the compounds according to the invention, the said preferred features can also be selected among the more preferred features of each of X, $A^1$, $A^2$, Y, $Het^1$, $Het^2$, R and Q; so as to form most preferred subclasses of compounds according to the invention.

The present invention also relates to a process for the preparation of compounds of formula (I). Thus, according to a further aspect of the present invention, there is a provided process P1 for the preparation of compounds of formula (I), as herein-defined, as illustrated by the following reaction scheme:

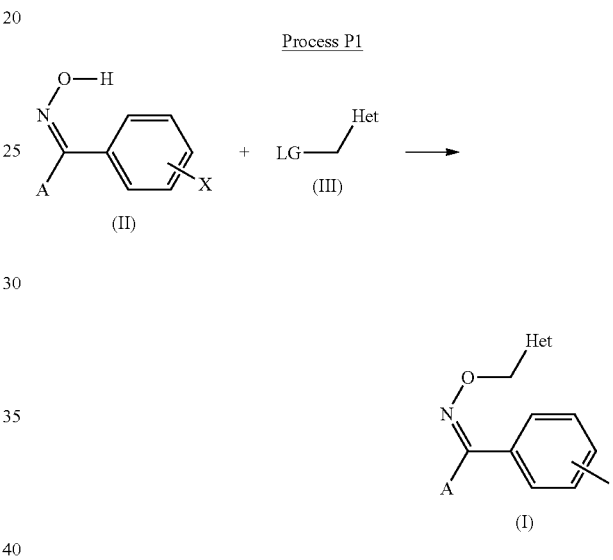

wherein A, X, Z, Q and Het are as herein-defined and LG represents a leaving group. Suitable leaving groups can be selected in the list consisting of a halogen atom or other customary nucleofugal groups such as triflate, mesylate or tosylate.

For the compounds of formula (Ia) according to the invention, process P1 according to the invention can be completed by a further step comprising the additional modification of this group, notably by a reaction of acylation or alkoxycarbonylation to yield to a compound of formula (Ib), according to known methods. In such a case there is provided a process P2 according to the invention and such a process P2 can be illustrated by the following reaction scheme:

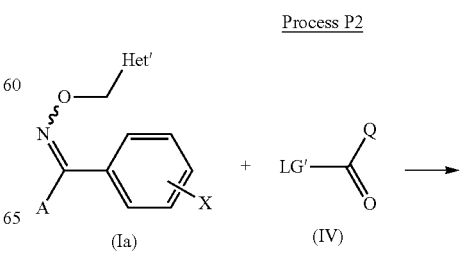

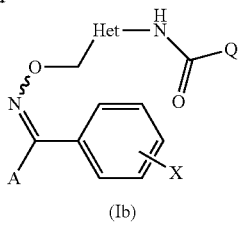

(Ib)

wherein A, X, Q and Het are as herein-defined and LG¹ represents a leaving group. Het' represents a pyridyl group of formula (Het'¹) or a thiazolyl group of formula (Het'²):

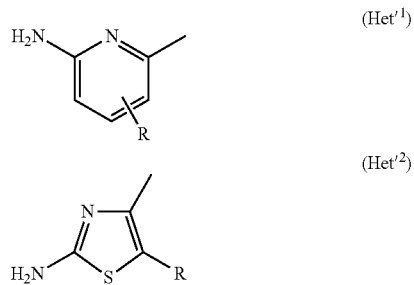

wherein R is as herein-defined.

Suitable leaving groups can be selected in the list consisting of a halogen atom or other customary nucleofugal groups such as alcoolate, hydroxide or cyanide.

For the compounds of formula (Ia), carrying out process P2 would previously require a deprotection step in order to yield the amino group. Amino-protecting groups and related methods of cleavage thereof are well-known to the ordinary skilled man in the art.

According to the invention, processes P1 and P2 can be performed if appropriate in the presence of a solvent and if appropriate in the presence of a base.

According to the invention, processes P1 and P2 can be performed if appropriate in the presence of a catalyst. Suitable catalyst can be selected in the list consisting of 4-dimethyl-aminopyridine, 1-hydroxy-benzotriazole or dimethyl-formamide.

In case LG' represents a hydroxy group, process P2 according to the present invention can be performed in the presence of condensing agent. Suitable condensing agent can be selected in the list consisting of acid halide former, such as phosgene, phosphorous tri-bro-mide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromo-tripyrrolidino-phosphonium-hexafluorophosphate.

Suitable solvents for carrying out processes P1 and P2 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

Suitable bases for carrying out processes P1 and P2 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

When carrying out processes P1 and P2 according to the invention, the reaction temperature can independently be varied within a relatively wide range.

Generally, process P1 according to the invention is carried out at temperatures between −20° C. and 160° C.

Processes P1 and P2 according to the invention are generally independently carried out under atmospheric pressure. However, it is also possible to operate under elevated or reduced pressure.

When carrying out process P1 according to the invention, generally 1 mol or an excess of derivative of formula Het-CH₂-LG and from 1 to 3 mol of base are employed per mole of hydroximoyl tetrazole of formula (II). It is also possible to employ the reaction components in other ratios.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that can still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesised.

When A represents a substituent of formula A¹, as herein-described, the compounds of formula (II), useful as a starting material, can be prepared, for example, by reacting hydroxylamine with the corresponding ketones that can be prepared, for example, according to the method described by R. Raap (*Can. J. Chem.* 1971, 49, 2139) by addition of a tetrazolyl lithium species to esters of formula

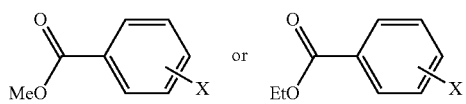

or any of their suitable synthetic equivalents like, for example:

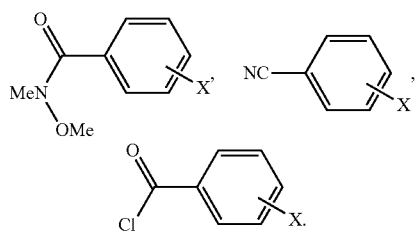

When A represents a substituent of formula $A^2$, as hereindescribed, the compounds of general formula (II) useful as a starting material, can be prepared, for example, from oximes of formula

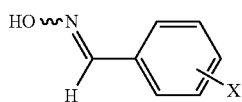

and 5-substituted tetrazole according to the method described by J. Plenkiewicz et al. (*Bull. Soc. Chim. Belg.* 1987, 96, 675).

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic organic or inorganic compound with which the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols and derivatives of the above compounds containing sulphate, sulphonate and phosphate functions. The presence of at least one surfactant is generally essential if the active compound and/or the inert support are water-insoluble and if the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity. The mixtures with other fungicide compounds are particularly advantageous. The composition according to the invention comprising a mixture of a compound of formula (I) with a bactericide compound can also be particularly advantageous.

Examples of suitable fungicide mixing partners can be selected in the following lists:

(1) Inhibitors of the nucleic acid synthesis, for example benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.

(2) Inhibitors of the mitosis and cell division, for example benomyl, carbendazim, chlorfenazole, diethofencarb, ethaboxam, fuberidazole, pencycuron, thiabendazole, thiophanate, thiophanate-methyl and zoxamide.

(3) Inhibitors of the respiration, for example diflumetorim as CI-respiration inhibitor; bixafen, boscalid, carboxin, fenfuram, flutolanil, fluopyram, furametpyr, furmecyclox, isopyrazam (mixture of syn-epimeric racemate 1RS,4SR, 9RS and anti-epimeric racemate 1RS,4SR,9SR), isopyrazam (syn epimeric racemate 1 RS,4SR,9RS), isopyrazam (syn-epimeric enantiomer 1R,4S,9R), isopyrazam (syn-epimeric enantiomer 1S,4R,9S), isopyrazam (anti-epimeric racemate 1 RS,4SR,9SR), isopyrazam (anti-epimeric enantiomer 1R,4S, 9S), isopyrazam (anti-epimeric enantiomer 1S,4R,9R), mepronil, oxycarboxin, penflufen, penthiopyrad, sedaxane, thifluzamide as CII-respiration inhibitor; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyraoxystrobin, pyrametostrobin, pyribencarb, trifloxystrobin as CIII-respiration inhibitor.

(4) Compounds capable to act as an uncoupler, like for example binapacryl, dinocap, fluazinam and meptyldinocap.

(5) Inhibitors of the ATP production, for example fentin acetate, fentin chloride, fentin hydroxide, and silthiofam.

(6) Inhibitors of the amino acid and/or protein biosynthesis, for example andoprim, blasticidin-S, cyprodinil, kasugamycin, kasugamycin hydrochloride hydrate, mepanipyrim and pyrimethanil.

(7) Inhibitors of the signal transduction, for example fenpiclonil, fludioxonil and quinoxyfen.

(8) Inhibitors of the lipid and membrane synthesis, for example biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin.

(9) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole.

(10) Inhibitors of the cell wall synthesis, for example benthiavalicarb, dimethomorph, flumorph, iprovalicarb, mandipropamid, polyoxins, polyoxorim, prothiocarb, validamycin A, and valifenalate.

(11) Inhibitors of the melanine biosynthesis, for example carpropamid, diclocymet, fenoxanil, phthalide, pyroquilon and tricyclazole.

(12) Compounds capable to induce a host defence, like for example acibenzolar-S-methyl, probenazole, and tiadinil.

(13) Compounds capable to have a multisite action, like for example bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxinecopper, propamidine, propineb, sulphur and sulphur preparations including calcium polysulphide, thiram, tolylfluanid, zineb and ziram.

(14) Further compounds like for example 2,3-dibutyl-6-chlorothieno[2,3-d]pyrimidin-4(3H)-one, ethyl (2Z)-3-amino-2-cyano-3-phenylprop-2-enoate, N-[2-(1,3-dimethylbutyl) phenyl]-5-fluoro-1,3-dimethyl-1H-pyrazole-4-carboxamide, 3-(difluoromethyl)-1-methyl-N-(3',4',5'-trifluorobiphenyl-2-yl)-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, (2E)-2-(2-{[6-(3-chloro-2-methylphenoxy)-5-fluoropyrimidin-4-yl]oxy}phenyl)-2-(methoxyimino)-N-methylethanamide, (2E)-2-{2-[({[(2E, 3E)-4-(2,6-dichlorophenyl)but-3-en-2-ylidene]amino}oxy) methyl]phenyl}-2-(methoxyimino)-N-methylethanamide, 2-chloro-N-(1,1,3-trimethyl-2,3-dihydro-1H-inden-4-yl)pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-1-[3-(trifluoromethyl)phenyl] ethylidene}amino)oxy]methyl}phenyl)-2,4-dihydro-3H-1, 2,4-triazol-3-one, (2E)-2-(methoxyimino)-N-methyl-2-(2-{[({(1E)-1-[3-(trifluoromethyl)phenyl] ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl] oxy}phenyl)ethylidene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy] phenyl}imidoformamide, N'-{5-(difluoromethyl)-2-methyl-4-[3-(trimethylsilyl)propoxy]phenyl}-N-ethyl-N-methylimidoformamide, O-{1-[(4-methoxyphenoxy) methyl]-2,2-dimethylpropyl}1H-imidazole-1-carbothioate, N-[2-(4-{[3-(4-chlorophenyl)prop-2-yn-1-yl]oxy}-3-methoxyphenyl)ethyl]-N²-(methylsulfonyl)valinamide, 5-chloro-7-(4-methylpiperidin-1-yl)-6-(2,4,6-trifluorophenyl)[1,2,4] triazolo[1,5-a]pyrimidine, 5-amino-1,3,4-thiadiazole-2-thiol, propamocarb-fosetyl, 1-[(4-methoxyphenoxy) methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-phenylphenol and salts, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, quinolin-8-ol, quinolin-8-ol sulfate (2:1) (salt), tebufloquin, 5-methyl-6-octyl-3,7-dihydro[1,2,4]triazolo[1, 5-a]pyrimidin-7-amine, 5-ethyl-6-octyl-3,7-dihydro[1,2,4] triazolo[1,5-a]pyrimidin-7-amine, ametoctradin, benthiazole, bethoxazin, capsimycin, carvone, chinomethionat, chloroneb, cufraneb, cyflufenamid, cymoxanil, cyprosulfamide, dazomet, debacarb, dichlorophen, diclomezine, dichloran, difenzoquat, difenzoquat methylsulphate, diphenylamine, ecomate, ferimzone, flumetover, fluopicolide, fluoroimide, flusulfamide, flutianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl isothiocyanate, metrafenone, (5-chloro-2-methoxy-4-methylpyridin-3-yl)(2,3,4-trimethoxy-6-methylphenyl)methanone, mildiomycin, tolnifanide, N-(4-chlorobenzyl)-3-[3-methoxy-4-(prop-2-yn-1-yloxy)phenyl]propanamide, N-[(4-chlorophenyl)(cyano) methyl]-3-[3-methoxy-4-(prop-2-yn-1-yloxy)phenyl] propanamide, N-[(5-bromo-3-chloropyridin-2-yl)methyl]-2, 4-dichloropyridine-3-carboxamide, N-[1-(5-bromo-3- chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropylmethoxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and salts, phenazine-1-carboxylic acid, phenothrin, phosphorous acid and its salts, propamocarb fosetylate, propanosine-sodium, proquinazid, pyrrolnitrine, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'-phenyl-N'-prop-2-yn-1-ylthiophene-2-sulfonohydrazide, zarilamid, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, 3-(difluoromethyl)-N-[4-fluoro-2-(1,1,2,3,3,3-hexafluoropropoxy)phenyl]-1-methyl-1H-pyrazole-4-carboxamide and pentyl {6-[({[(1-methyl-1H-tetrazol-5-yl)(phenyl)methylidene]amino}oxy)methyl]pyridin-2-yl}carbamate.

According to another object of the present invention, there is provided a method for controlling the phytopathogenic fungi of plants, crops or seeds, characterized in that an agronomically effective and substantially non-phytotoxic quantity of a pesticide composition according to the invention is applied as seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumice, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to grow.

The expression "are applied to the plants to be treated" is understood to mean, for the purposes of the present invention, that the pesticide composition which is the subject of the invention can be applied by means of various methods of treatment such as:
  spraying onto the aerial parts of the said plants a liquid comprising one of the said compositions,
  dusting, the incorporation into the soil of granules or powders, spraying, around the said plants and in the case of trees injection or daubing,
  coating or film-coating the seeds of the said plants with the aid of a plant-protection mixture comprising one of the said compositions.

The method according to the invention can either be a curing, preventing or eradicating method. In this method, a composition used can be prepared beforehand by mixing the two or more active compounds according to the invention.

According to an alternative of such a method, it is also possible to apply simultaneously, successively or separately compounds (A) and (B) so as to have the conjugated (A)/(B) effects, of distinct compositions each containing one of the two or three active ingredients (A) or (B).

The dose of active compound usually applied in the method of treatment according to the invention is generally and advantageously
  for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;
  for seed treatment: from 2 to 200 g per 100 kilogram of seed, preferably from 3 to 150 g per 100 kilogram of seed;
  for soil treatment: from 0.1 to 10,000 g/ha, preferably from 1 to 5,000 g/ha.

The doses herein indicated are given as illustrative Examples of method according to the invention. A person skilled in the art will know how to adapt the application doses, notably according to the nature of the plant or crop to be treated.

Under specific conditions, for example according to the nature of the phytopathogenic fungus to be treated or controlled, a lower dose can offer adequate protection. Certain climatic conditions, resistance or other factors like the nature of the phytopathogenic fungi or the degree of infestation, for example, of the plants with these fungi, can require higher doses of combined active ingredients. The optimum dose usually depends on several factors, for example on the type of phytopathogenic fungus to be treated, on the type or level of development of the infested plant, on the density of vegetation or alternatively on the method of application.

Without it being limiting, the crop treated with the pesticide composition or combination according to the invention is, for example, grapevine, but this could be cereals, vegetables, lucerne, soybean, market garden crops, turf, wood, tree or horticultural plants.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

Among the plants that can be protected by the method according to the invention, mention can be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

The composition according to the invention can also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties or genes for improving the agronomic quality of the modified plant.

The composition according to the invention can also be used against fungal diseases liable to grow on or inside timber. The term "timber" means all types of species of wood and all types of working of this wood intended for construction, for example solid wood, high-density wood, laminated wood and plywood. The method for treating timber according to the invention mainly consists in contacting one or more compounds according to the invention or a composition according to the invention; this includes for example direct application, spraying, dipping, injection or any other suitable means.

Among the diseases of plants or crops that can be controlled by the method according to the invention, mention can be made of:

Powdery mildew diseases such as:
  Blumeria diseases, caused for example by Blumeria graminis;
  Podosphaera diseases, caused for example by Podosphaera leucotricha;
  Sphaerotheca diseases, caused for example by Sphaerotheca fuliginea;
  Uncinula diseases, caused for example by Uncinula necator;
Rust diseases such as:
  Gymnosporangium diseases, caused for example by Gymnosporangium sabinae;
  Hemileia diseases, caused for example by Hemileia vastatrix;
  Phakopsora diseases, caused for example by Phakopsora pachyrhizi or Phakopsora meibomiae;
  Puccinia diseases, caused for example by Puccinia recondita;
  Uromyces diseases, caused for example by Uromyces appendiculatus;
Oomycete diseases such as:
  Bremia diseases, caused for example by Bremia lactucae;
  Peronospora diseases, caused for example by Peronospora pisi or P. brassicae;
  Phytophthora diseases, caused for example by Phytophthora infestans;
  Plasmopara diseases, caused for example by Plasmopara viticola;
  Pseudoperonospora diseases, caused for example by Pseudoperonospora humuli or Pseudoperonospora cubensis;
  Pythium diseases, caused for example by Pythium ultimum;
Leafspot, leaf blotch and leaf blight diseases such as:
  Alternaria diseases, caused for example by Alternaria solani;
  Cercospora diseases, caused for example by Cercospora beticola;
  Cladiosporum diseases, caused for example by Cladiosporium cucumerinum;
  Cochliobolus diseases, caused for example by Cochliobolus sativus;
  Colletotrichum diseases, caused for example by Colletotrichum lindemuthanium;
  Cycloconium diseases, caused for example by Cycloconium oleaginum;
  Diaporthe diseases, caused for example by Diaporthe citri;
  Elsinoe diseases, caused for example by Elsinoe fawcettii;
  Gloeosporium diseases, caused for example by Gloeosporium laeticolor;
  Glomerella diseases, caused for example by Glomerella cingulata;
  Guignardia diseases, caused for example by Guignardia bidwelli;
  Leptosphaeria diseases, caused for example by Leptosphaeria maculans; Leptosphaeria nodorum;
  Magnaporthe diseases, caused for example by Magnaporthe grisea;
  Mycosphaerella diseases, caused for example by Mycosphaerella graminicola; Mycosphaerella arachidicola; Mycosphaerella fijiensis;
  Phaeosphaeria diseases, caused for example by Phaeosphaeria nodorum;
  Pyrenophora diseases, caused for example by Pyrenophora teres;
  Ramularia diseases, caused for example by Ramularia collo-cygni;
  Rhynchosporium diseases, caused for example by Rhynchosporium secalis;
  Septoria diseases, caused for example by Septoria apii or Septoria lycopercisi;
  Typhula diseases, caused for example by Typhula incamata;
  Venturia diseases, caused for example by Venturia inaequalis;
Root and stem diseases such as:
  Corticium diseases, caused for example by Corticium graminearum;
  Fusarium diseases, caused for example by Fusarium oxysporum;
  Gaeumannomyces diseases, caused for example by Gaeumannomyces graminis;
  Rhizoctonia diseases, caused for example by Rhizoctonia solani;
  Tapesia diseases, caused for example by Tapesia acuformis;
  Thielaviopsis diseases, caused for example by Thielaviopsis basicola;
Ear and panicle diseases such as:
  Alternaria diseases, caused for example by Alternaria spp.;
  Aspergillus diseases, caused for example by Aspergillus flavus;
  Cladosporium diseases, caused for example by Cladosporium spp.;
  Claviceps diseases, caused for example by Claviceps purpurea;
  Fusarium diseases, caused for example by Fusarium culmorum;
  Gibberella diseases, caused for example by Gibberella zeae;
  Monographella diseases, caused for example by Monographella nivalis;
Smut and bunt diseases such as:
  Sphacelotheca diseases, caused for example by Sphacelotheca reiliana;
  Tilletia diseases, caused for example by Tilletia caries;
  Urocystis diseases, caused for example by Urocystis occulta;
  Ustilago diseases, caused for example by Ustilago nuda;
Fruit rot and mould diseases such as:

*Aspergillus* diseases, caused for example by *Aspergillus flavus;*

*Botrytis* diseases, caused for example by *Botrytis cinerea;*

*Penicillium* diseases, caused for example by *Penicillium expansum;*

*Sclerotinia* diseases, caused for example by *Sclerotinia sclerotiorum;*

*Verticilium* diseases, caused for example by *Verticilium alboatrum;*

Seed and soilborne decay, mould, wilt, rot and damping-off diseases:

*Alternaria* diseases, caused for example by *Alternaria brassicicola*

*Aphanomyces* diseases, caused for example by *Aphanomyces euteiches*

*Ascochyta* diseases, caused for example by *Ascochyta lentis*

*Aspergillus* diseases, caused for example by *Aspergillus flavus*

*Cladosporium* diseases, caused for example by *Cladosporium herbarum*

*Cochliobolus* diseases, caused for example by *Cochliobolus sativus*

(Conidiaform: *Drechslera, Bipolaris* Syn: *Helminthosporium*);

*Colletotrichum* diseases, caused for example by *Colletotrichum coccodes;*

*Fusarium* diseases, caused for example by *Fusarium culmorum;*

*Gibberella* diseases, caused for example by *Gibberella zeae;*

*Macrophomina* diseases, caused for example by *Macrophomina phaseolina*

*Monographella* diseases, caused for example by *Monographella nivalis;*

*Penicillium* diseases, caused for example by *Penicillium expansum*

*Phoma* diseases, caused for example by *Phoma lingam*

*Phomopsis* diseases, caused for example by *Phomopsis sojae;*

*Phytophthora* diseases, caused for example by *Phytophthora cactorum;*

*Pyrenophora* diseases, caused for example by *Pyrenophora graminea*

*Pyricularia* diseases, caused for example by *Pyricularia oryzae;*

*Pythium* diseases, caused for example by *Pythium ultimum;*

*Rhizoctonia* diseases, caused for example by *Rhizoctonia solani;*

*Rhizopus* diseases, caused for example by *Rhizopus oryzae*

*Sclerotium* diseases, caused for example by *Sclerotium rolfsii;*

*Septoria* diseases, caused for example by *Septoria nodorum;*

*Typhula* diseases, caused for example by *Typhula incarnata;*

*Verticillium* diseases, caused for example by *Verticillium dahliae;*

Canker, broom and dieback diseases such as:

*Nectria* diseases, caused for example by *Nectria gafiigena;*

Blight diseases such as:

*Monilinia* diseases, caused for example by *Monilinia taxa;*

Leaf blister or leaf curl diseases such as:

*Taphrina* diseases, caused for example by *Taphrina deformans;*

Decline diseases of wooden plants such as:

Esca diseases, caused for example by *Phaemoniella clamydospora;*

*Eutypa* dyeback, caused for example by *Eutypa late;*

Dutch elm disease, caused for example by *Ceratocystsc ulmi;*

Diseases of flowers and Seeds such as:

*Botrytis* diseases, caused for example by *Botrytis cinerea;*

Diseases of tubers such as:

*Rhizoctonia* diseases, caused for example by *Rhizoctonia solani*

*Helminthosporium* diseases, caused for example by *Helminthosporium solani.*

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229, 072). However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a Petunia EPSPS (Shah et al., Science (1986), 233, 478-481), a Tomato EPSPS (Gasser et al., J. Biol. Chem. (1988), 263, 4280-4289), or an *Eleusine* EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxido-reductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. No. 5,605,011, U.S. Pat. No. 5,378,824, U.S. Pat. No. 5,141,870, and U.S. Pat. No. 5,013,659. The production of sulfonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 1997/41218, for sugar beet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., *Nat. Biotechnol.* (2001), 19, 668-72; Schnepf et al., Applied Environm. Microbiol. (2006), 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A. 105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants as described in WO 2000/004173 or WO2006/045633 or PCT/EP07/004,142.

b. plants which contain a stress tolerance enhancing transgene capable of reducing the expression and/or the activity of the PARG encoding genes of the plants or plants cells, as described e.g. in WO 2004/090140.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO 2006/133827 or PCT/EP07/002,433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO99/58688, WO 1999/58690, WO 1999/58654, WO 2000/008184, WO 2000/008185, WO 2000/008175, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026, WO 1997/20936.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 1996/001904, WO 1996/021023, WO 1998/039460, and WO 1999/024593, plants producing alpha 1,4 glucans as disclosed in WO 1995/031553, US 2002/031826, U.S. Pat. No. 6,284,479, U.S. Pat. No. 5,712,107, WO 1997/047806, WO 1997/047807, WO 1997/047808 and WO 2000/014249, plants producing alpha-1,6 branched alpha-1,4-glucans, as disclosed in WO 2000/73422, plants producing alternan, as disclosed in WO 2000/047727, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006/304779, and WO 2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 1998/000549 b) Plants, such as cotton plants, containing an altered form of rsw2 or rsw3 homologous nucleic acids as described in WO2004/053219 c) Plants, such as cotton plants, with increased expression of sucrose phosphate synthase as described in WO 2001/017333 d) Plants, such as cotton plants, with increased expression of sucrose synthase as described in WO02/45485 e) Plants, such as cotton plants, wherein the timing of the plasmodesmatal gating at the basis of the fiber cell is altered, e.g. through downregulation of fiberselective β 1,3-glucanase as described in WO2005/017157 f) Plants, such as cotton plants, having fibers with altered reactivity, e.g. through the expression of N-acteylglucosaminetransferase gene including nodC and chitin-synthase genes as described in WO2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947 b) Plants such as oilseed rape plants, producing oil having a low linolenic acid content as described in U.S. Pat. No. 6,270,828, U.S. Pat. No. 6,169,190 or U.S. Pat. No. 5,965,755 c) Plant such as oilseed rape plants, producing oil having a low level of saturated fatty acids as described e.g. in U.S. Pat. No. 5,434,283

Particularly useful transgenic plants which may be treated according to the invention are plants which comprise one or more genes which encode one or more toxins, such as the following which are sold under the trade names YIELD GARD$_3$ (for example maize, cotton, soya beans), KnockOut$_3$ (for example maize), BiteGard$_3$ (for example maize), Bt-Xtra$_3$ (for example maize), StarLink$_3$ (for example maize), Bollgard$_3$ (cotton), Nucotn$_3$ (cotton), Nucotn 33B® (cotton), NatureGard$_3$ (for example maize), Protecta$_3$ and NewLeaf$_3$ (potato). Examples of herbicide-tolerant plants which may be mentioned are maize varieties, cotton varieties and soya bean varieties which are sold under the trade names Roundup Ready$_3$ (tolerance to glyphosate, for example maize, cotton, soya bean), Liberty Link$_3$ (tolerance to phosphinotricin, for example oilseed rape), IMI$_3$ (tolerance to imidazolinones) and STS$_3$ (tolerance to sulphonylureas, for example maize).

Herbicide-resistant plants (plants bred in a conventional manner for herbicide tolerance) which may be mentioned include the varieties sold under the name Clearfield₃ (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

The compounds according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The various aspects of the invention will now be illustrated with reference to the following table 1 of compound examples and the following preparation or efficacy examples.

The following table 1 illustrates in a non limiting manner examples of compounds according to the invention.

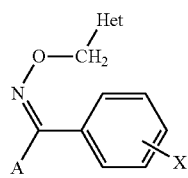
(I)

In table 1, we use the following abbreviations for specified claimed elements "A", "Het" and "Z" (as specification of "Q") of the generic structure (I) of the invention:

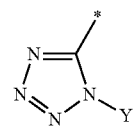
(A¹)

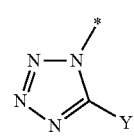
(A²)

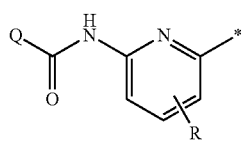
(Het¹)

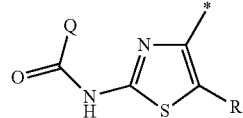
(Het²)

Specifications of Q: (Z), (Z¹), (Z²), (Z³)

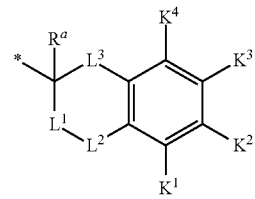
(Z)

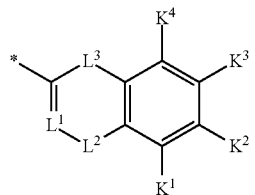
(Z¹)

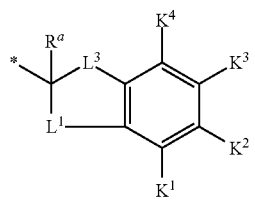
(Z²)

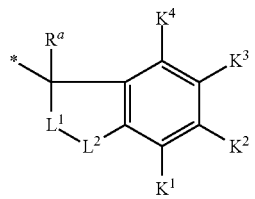
(Z³)

In case (Z¹)$R^a$ is empty. In case (Z²)$L^2$ is empty. "*" marks binding site.

TABLE 1

| Example | A | Het | R | Q | $L^2$ | $L^1$ | $R^a$ | $CR^a$ | $L^3$ | $K^1$ | $K^2$ | $K^3$ | $K^4$ | Phenyl-X | Y | logp | MW measured |
|---|---|---|---|---|---|---|---|---|---|---|---|---|---|---|---|---|---|
| 1 | A¹ | Het¹ | H | Z | CO | CH₂ | H | CH | O | H | F | H | H | phenyl | CH₃ | 3.46 | 502 |
| 2 | A¹ | Het¹ | H | Z | CH₂ | CH₂ | H | CH | O | H | I | H | H | phenyl | CH₃ | 4.7 | 596 |
| 3 | A¹ | Het¹ | H | Z | CH₂ | CH₂ | H | CH | O | H | H | H | MeO | phenyl | CH₃ | 3.92 | 500 |
| 4 | A¹ | Het¹ | H | Z | CH₂ | CH₂ | H | CH | O | H | F | H | H | phenyl | CH₃ | 4.01 | 488 |
| 5 | A¹ | Het¹ | H | Z | CH₂ | CH₂ | H | CH | O | H | H | H | H | phenyl | CH₃ | 4.01 | 470 |
| 6 | A¹ | Het¹ | H | Z | O | CH₂ | H | CH | O | H | H | tBu | H | phenyl | CH₃ | 4.92 | 528 |
| 7 | A¹ | Het¹ | H | Z | O | CH₂ | H | CH | O | H | H | CH₃ | H | phenyl | CH₃ | 4.03 | 486 |

TABLE 1-continued

| Example | A | Het | R | Q | $L^2$ | $L^1$ | $R^a$ | $CR^a$ | $L^3$ | $K^1$ | $K^2$ | $K^3$ | $K^4$ | Phenyl-X | Y | logp | MW measured |
|---|---|---|---|---|---|---|---|---|---|---|---|---|---|---|---|---|---|
| 8 | $A^1$ | $Het^1$ | H | Z | O | $CH_2$ | H | CH | O | H | H | H | $CH_3$ | phenyl | $CH_3$ | 4.08 | 486 |
| 9 | $A^1$ | $Het^1$ | H | Z | O | $CH_2$ | H | CH | O | H | H | H | H | phenyl | $CH_3$ | 3.69 | 472 |
| 10 | $A^1$ | $Het^2$ | H | Z | $CH_2$ | $CH_2$ | H | CH | O | H | H | H | H | phenyl | $CH_3$ | 3.78 | 476 |
| 11 | $A^1$ | $Het^2$ | H | Z | O | $CH_2$ | H | CH | O | H | H | H | H | phenyl | $CH_3$ | 3.46 | 478 |
| 12 | $A^1$ | $Het^2$ | H | Z | O | $CH_2$ | H | CH | O | H | H | $CH_3$ | H | phenyl | $CH_3$ | 3.78 | 492 |
| 13 | $A^1$ | $Het^2$ | H | Z | O | $CH_2$ | H | CH | O | H | H | H | $CH_3$ | phenyl | $CH_3$ | 3.83 | 492 |
| 14 | $A^1$ | $Het^2$ | H | Z | O | $CH_2$ | H | CH | O | H | H | H | H | phenyl | $CH_3$ | 3.46 | 478 |
| 15 | $A^1$ | $Het^2$ | H | Z | O | $CH_2$ | H | CH | O | H | H | tBu | H | phenyl | $CH_3$ | 4.62 | 534 |
| 16 | $A^1$ | $Het^2$ | H | Z | CO | $CH_2$ | H | CH | O | H | F | H | H | phenyl | $CH_3$ | 3.29 | 508 |
| 17 | $A^1$ | $Het^2$ | H | Z | $CH_2$ | $CH_2$ | H | CH | O | H | I | H | H | phenyl | $CH_3$ | 4.44 | 602 |
| 18 | $A^1$ | $Het^2$ | H | Z | $CH_2$ | $CH_2$ | H | CH | O | H | H | H | MeO | phenyl | $CH_3$ | 3.64 | 506 |
| 19 | $A^1$ | $Het^2$ | H | Z | $CH_2$ | $CH_2$ | H | CH | O | H | F | H | H | phenyl | $CH_3$ | 3.8 | 494 |
| 20 | $A^1$ | $Het^2$ | H | Z | $CH_2$ | $CH_2$ | H | CH | O | H | H | H | H | phenyl | $CH_3$ | 3.78 | 476 |
| 21 | $A^2$ | $Het^1$ | H | Z | $CH_2$ | $CH_2$ | H | CH | O | H | I | H | H | phenyl | $CH_3$ | 4.81 | 596 |
| 22 | $A^2$ | $Het^1$ | H | Z | $CH_2$ | $CH_2$ | H | CH | O | H | H | H | MeO | phenyl | $CH_3$ | 3.99 | 500 |
| 23 | $A^2$ | $Het^1$ | H | Z | $CH_2$ | $CH_2$ | H | CH | O | H | F | H | H | phenyl | $CH_3$ | 4.11 | 488 |
| 24 | $A^2$ | $Het^1$ | H | Z | $CH_2$ | $CH_2$ | H | CH | O | H | H | H | H | phenyl | $CH_3$ | 4.08 | 470 |
| 25 | $A^2$ | $Het^1$ | H | Z | O | $CH_2$ | H | CH | O | H | H | tBu | H | phenyl | $CH_3$ | 5.03 | 528 |
| 26 | $A^2$ | $Het^1$ | H | Z | O | $CH_2$ | H | CH | O | H | H | $CH_3$ | H | phenyl | $CH_3$ | 4.11 | 486 |
| 27 | $A^2$ | $Het^1$ | H | Z | O | $CH_2$ | H | CH | O | H | H | H | $CH_3$ | phenyl | $CH_3$ | 4.15 | 486 |
| 28 | $A^2$ | $Het^1$ | H | Z | O | $CH_2$ | H | CH | O | H | H | H | H | phenyl | $CH_3$ | 3.78 | 472 |
| 29 | $A^2$ | $Het^1$ | H | Z | CO | $CH_2$ | H | CH | O | H | F | H | H | phenyl | $CH_3$ | 3.53 | 502 |
| 30 | $A^2$ | $Het^2$ | H | Z | $CH_2$ | $CH_2$ | H | CH | O | H | H | H | MeO | phenyl | $CH_3$ | 3.69 | 506 |
| 31 | $A^2$ | $Het^2$ | H | Z | $CH_2$ | $CH_2$ | H | CH | O | H | F | H | H | phenyl | $CH_3$ | 3.87 | 494 |
| 32 | $A^2$ | $Het^2$ | H | Z | $CH_2$ | $CH_2$ | H | CH | O | H | H | H | H | phenyl | $CH_3$ | 3.83 | 476 |
| 33 | $A^2$ | $Het^2$ | H | Z | O | $CH_2$ | H | CH | O | H | H | tBu | H | phenyl | $CH_3$ | 4.67 | 534 |
| 34 | $A^2$ | $Het^2$ | H | Z | O | $CH_2$ | H | CH | O | H | H | $CH_3$ | H | phenyl | $CH_3$ | 3.83 | 492 |
| 35 | $A^2$ | $Het^2$ | H | Z | O | $CH_2$ | H | CH | O | H | H | H | $CH_3$ | phenyl | $CH_3$ | 3.87 | 492 |
| 36 | $A^2$ | $Het^2$ | H | Z | O | $CH_2$ | H | CH | O | H | H | H | H | phenyl | $CH_3$ | 3.51 | 478 |
| 37 | $A^2$ | $Het^2$ | H | Z | CO | $CH_2$ | H | CH | O | H | F | H | H | phenyl | $CH_3$ | 3.33 | 508 |
| 38 | $A^2$ | $Het^2$ | H | Z | $CH_2$ | $CH_2$ | H | CH | O | H | I | H | H | phenyl | $CH_3$ | 4.49 | 602 |
| 39 | $A^1$ | $Het^1$ | H | Z | $CH_2$ | $CH_2$ | H | CH | O | H | H | MeO | H | phenyl | $CH_3$ | 3.96 | 500 |
| 40 | $A^1$ | $Het^2$ | H | Z | $CH_2$ | $CH_2$ | H | CH | O | H | H | MeO | H | phenyl | $CH_3$ | 3.78 | 506 |
| 41 | $A^1$ | $Het^1$ | H | $Z^2$ |  | $CH_2$ | H | CH | O | H | H | H | H | phenyl | $CH_3$ | 3.67 | 456 |
| 42 | $A^1$ | $Het^2$ | H | $Z^2$ |  | $CH_2$ | H | CH | O | H | H | H | H | phenyl | $CH_3$ | 3.39 | 462 |
| 43 | $A^2$ | $Het^1$ | H | $Z^1$ | CO | CH |  | C | O | H | H | H | H | phenyl | $CH_3$ | 3.33 | 482 |
| 44 | $A^2$ | $Het^2$ | H | $Z^1$ | CO | CH |  | C | O | H | H | H | H | phenyl | $CH_3$ | 3.21 | 488 |
| 45 | $A^2$ | $Het^2$ | H | $Z^2$ |  | $CH_2$ | H | CH | O | H | H | H | H | phenyl | $CH_3$ | 3.44 | 462 |
| 46 | $A^2$ | $Het^2$ | H | $Z^2$ |  | O | H | CH | O | H | H | H | H | phenyl | $CH_3$ | 3.31 | 464 |
| 47 | $A^1$ | $Het^2$ | H | $Z^1$ | CO | CH |  | C | O | H | H | H | H | phenyl | $CH_3$ | 3.17 | 488 |
| 48 | $A^1$ | $Het^2$ | H | $Z^2$ |  | O | H | CH | O | H | H | H | H | phenyl | $CH_3$ | 3.29 | 464 |
| 49 | $A^1$ | $Het^2$ | H | $Z^3$ | O | $CH_2$ | H | CH |  | H | H | H | H | phenyl | $CH_3$ | 3.19 | 462 |
| 50 | $A^1$ | $Het^1$ | 3-Br | Z | $CH_2$ | $CH_2$ | H | CH | O | H | H | H | H | phenyl | $CH_3$ | 4.61 |  |
| 51 | $A^1$ | $Het^1$ | 3-Br | Z | O | $CH_2$ | H | CH | O | H | H | H | H | phenyl | $CH_3$ | 4.24 |  |
| 52 | $A^1$ | $Het^1$ | 5-F | Z | $CH_2$ | $CH_2$ | H | CH | O | H | H | H | H | phenyl | $CH_3$ |  |  |
| 53 | $A^1$ | $Het^1$ | 5-F | Z | O | $CH_2$ | H | CH | O | H | H | H | H | phenyl | $CH_3$ |  |  |
| 54 | $A^1$ | $Het^1$ | 5-Cl | Z | $CH_2$ | $CH_2$ | H | CH | O | H | H | H | H | phenyl | $CH_3$ | 4.49 |  |
| 55 | $A^1$ | $Het^1$ | 5-Cl | Z | O | $CH_2$ | H | CH | O | H | H | H | H | phenyl | $CH_3$ | 4.14 |  |
| 56 | $A^2$ | $Het^1$ | H | $Z^2$ |  | $CH_2$ | H | CH | O | H | H | H | H | phenyl | $CH_3$ | 3.71 | 456 |
| 57 | $A^2$ | $Het^1$ | H | $Z^2$ |  | O | H | CH | O | H | H | H | H | phenyl | $CH_3$ | 3.48 | 458 |
| 58 | $A^2$ | $Het^1$ | H | $Z^3$ | O | $CH_2$ | H | CH |  | H | H | H | H | phenyl | $CH_3$ | 3.39 | 456 |
| 59 | $A^1$ | $Het^1$ | H | $Z^1$ | CO | CH |  | C | O | H | H | H | H | phenyl | $CH_3$ | 3.27 | 482 |
| 60 | $A^1$ | $Het^1$ | H | $Z^2$ |  | O | H | CH | O | H | H | H | H | phenyl | $CH_3$ | 3.44 | 458 |
| 61 | $A^1$ | $Het^1$ | H | $Z^3$ | O | $CH_2$ | H | CH |  | H | H | H | H | phenyl | $CH_3$ | 3.37 | 456 |

Abbreviations: MeO = methoxy; Cl = chloro; F = fluoro; Br = bromo; tBu = tert-butyl;

Measurement of log P values was performed according EEC directive 79/831 Annex V.A8 by HPLC (High Performance Liquid Chromatography) on reversed phase columns with the following method:

measurement of LC-MS was done at pH 2.7 with 0.1% formic acid in water and with acetonitrile (contains 0.1% formic acid) as eluent with a linear gradient from 10% acetonitrile to 95% acetonitrile.

Calibration was done with not branched alkan2-ones (with 3 to 16 carbon atoms) with known log P-values (measurement of log P values using retention times with linear interpolation between successive alkanones). lambda-maX-values were determined using UV-spectra from 200 nm to 400 nm and the peak values of the chromatographic signals.

In table 1, M+H (or M H) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

In all examples of table 1 the M+1 peak was measured.

The following examples illustrate in a non-limiting manner the preparation and efficacy of the compounds of formula (I) according to the invention.

PREPARATION EXAMPLE 1

N-{4-[({[(1-methyl-1H-tetrazol-5-yl)(phenyl)methylene]amino}oxy)methyl]-1,3-thiazol-2-yl}chromane-2-carboxamide (Compound 10)

To a stirred solution of 4-[({[(1-methyl-1H-tetrazol-5-yl)(phenyl)methylene]amino}oxy)methyl]-1,3-thiazol-2-amine (200 mg, 0.63 mmol) in dimethylformamide (1.5 mL)

were added chromane-2-carboxylic acid (124 mg, 0.70 mmol) and 1H-benzotriazol-1-ol (94 mg, 0.70 mmol). The reaction mixture was poured at room temperature on a cartridge filled with 1.44 g of silica linked with N,N'-dicyclohexylcarbodiimide (loading: 1.05 mmol/g). After one night at room temperature, the cartridge was eluted with 1 mL of dimethylformamide. The filtrated solution was then poured on a cartridge filled with 1.5 g of basic alumina. After 2 hours of reaction a room temperature, the cartridge was rinsed twice with 10 mL of ethyl acetate. The combined filtrated solutions were evaporated in vacuo to yield a yellow oil. Purification on silica gel afforded of N-{4-[({[(1-methyl-1H-tetrazol-5-yl)(phenyl)methylene]amino}oxy)methyl]-1,3-thiazol-2-yl}chromane-2-carboxamide as a colorless oil [150 mg, yield 44%; HPLC/MS: nm/z=476 (M+H); log $P_{(HCOOH)}$=3.78].

PREPARATION EXAMPLE 2

N-{6-[({[(1-methyl-1H-tetrazol-5-yl)(phenyl)methylene]amino}oxy)methyl]pyridin-2-yl}-2,3-dihydro-1-benzofuran-2-carboxamide (Compound 41)

To a stirred solution of 6-[({[(1-methyl-1H-tetrazol-5-yl)(phenyl)methylene]amino}oxy)methyl]pyridin-2-amine (100 mg, 0.32 mmol) in dry dichloromethane (4 mL) under argon was added pyridine (39 μL, 0.48 mmol) at room temperature, followed after fifteen minutes by 2,3-dihydro-1-benzofuran-2-carbonyl chloride (88 mg, 0.48 mmol). The reaction mixture was stirred overnight at room temperature and quenched by filtration on bi-layer cartridge filled with 1.4 g of basic alumina and 1 g of silica. The cartridge was rinsed twice by 10 mL of dichloromethane. The combined filtrated solutions were evaporated in vacuo to yield a colorless oil. Purification on silica gel afforded of N-{6-[({[(1-methyl-1H-tetrazol-5-yl)(phenyl)methylene]amino}oxy)methyl]pyridin-2-yl}-2,3-dihydro-1-benzofuran-2-carboxamide as a colorless oil [150 mg, yield 96%; HPLC/MS: nm/z=456 (M+H); log $P_{(HCOOH)}$=3.67].

Example A

Phytophthora Test (Tomato)/Preventive

| Solvent: | 49 | parts by weight of N,N-Dimethylformamide |
| Emulsifier: | 1 | part by weight of Alkylarylpolyglycolether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Phytophthora infestans*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient:
Example Number [table 1] (Efficacy %):
1 (93%), 2 (95%), 3 (95%), 4 (95%), 5 (95%), 6 (93%), 7 (95%), 8 (95%), 9 (85%), 10 (100%), 11 (95%), 12 (95%), 13 (98%), 14 (90%), 15 (90%), 16 (93%), 17 (93%), 18 (95%), 19 (95%), 20 (93%), 21 (80%), 22 (80%), 23 (90%), 24 (93%), 25 (93%), 26 (95%), 27 (95%), 28 (98%), 29 (90%), 30 (95%), 31 (95%), 32 (95%), 33 (90%), 34 (95%), 35 (95%), 36 (95%), 37 (95%), 38 (95%), 39 (95%), 40 (98%), 41 (89%), 42 (89%), 43 (85%), 44 (95%), 45 (98%), 46 (75%), 47 (70%), 48 (80%), 56 (100%), 57 (88%), 59 (95%), 60 (95%), 60 (95%)

Example B

Plasmopara Test (Grapevines)/Preventive

| Solvent: | 24.5 | parts by weight of acetone |
| | 24.5 | parts by weight of dimethylacetamide |
| Emulsifier: | 1 | part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the untreated control, while an efficacy of 100% means that no disease is observed.

In this test the following compounds according to the invention showed efficacy of 70% or even higher at a concentration of 10 ppm of active ingredient.
Example Number [table 1] (Efficacy %):
5(89%), 7 (75%), 8 (87%), 9 (97%), 10 (100%), 11 (98%), 40 (96%), 41 (97%), 41 (91%), 42 (100%), 45 (96%), 56 (85%), 60 (97%).

Example C

Pythium Test (Cotton)/Seed Treatment

The test is performed under greenhouse conditions.

Cotton seeds, treated with the active compound or compound combinations, solved in N-methyl-2-pyrrolidon and diluted with water to the desired dosages, were sown in 6*6 cm pots containing 4 cm of a 1:1 mix of steamed field soil and sand.

Perlite was incubated with mycelium fragments of *Pythium ultimum*. 1 ml of infected perlite was scattered between the treated cotton seeds. Seeds were then covered by light expanded clay aggregate. Pots were incubated in the greenhouse 7 days at 20° C. and 80% relative humidity.

Assessment consisted of counting of emerged seedlings. 0% means an efficacy which corresponds to that of the control, while an efficacy of 100% means that all seedlings have emerged.

In this test the following compounds according to the invention showed an efficacy of 70% or even higher at a dosage of 10 g/dt seed of active ingredient.

Example Number [table 1] (Efficacy %):
10 (86%), 11 (77%), 41 (92%),

The invention claimed is:

1. A compound of formula (I)

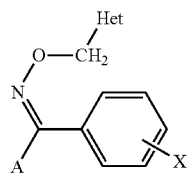

(I)

wherein
X represents a hydrogen atom, a halogen atom, substituted or non-substituted $C_1$-$C_8$-alkyl, a substituted or non-substituted $C_1$-$C_8$-alkoxy, a cyano group, a methanesulfonyl group, a nitro group, a trifluoromethyl group or an aryl group;
A represents a tetrazoyl group of formula ($A^1$) or ($A^2$):

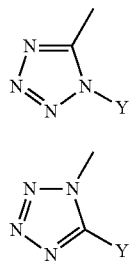

(A$^1$)

(A$^2$)

wherein Y represents substituted or non-substituted $C_1$-$C_8$-alkyl; and
Het represents a pyridyl group of formula (Het$^1$) or a thiazolyl group of formula (Het$^2$);

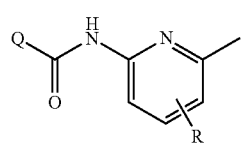

(Het$^1$)

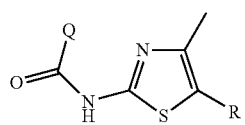

(Het$^2$)

wherein
R represents a hydrogen atom or a halogen atom and
Q represents a group of formula Z;

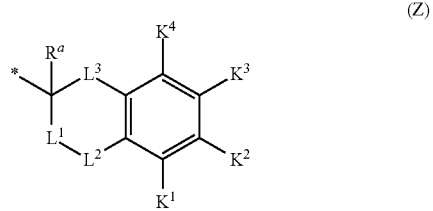

(Z)

wherein
$R^a$ represents a hydrogen atom, a substituted or non-substituted $C_1$-$C_8$-alkyl;
$L^1$ represents CH2;
$L^2$ represents CH2;
$L^3$ represents an oxygen atom;
$K^1$, $K^2$, $K^3$ and $K^4$ independently represent a hydrogen atom, a halogen atom, a nitro group, a hydroxy group, a cyano group, an isonitrile group, an amino group, a sulphanyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphanyl group, a formylamino group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphanyl, substituted or non-substituted $C_1$-$C_8$-halogenoalkylsulphanyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted $C_1$-$C_8$-alkylcarbamoyl, substituted or non-substituted di-$C_1$-$C_8$-alkylcarbamoyl, substituted or non-substituted $C_1$-$C_8$-alkoxycarbonyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphanyl, substituted or non-substituted benzylamino, substituted or non-substituted phenoxy, substituted or non-substituted phenylsulphanyl, substituted or non-substituted phenylamino, substituted or non-substituted aryl, substituted or non-substituted heterocyclyl, substituted or non-substituted tri($C_1$-$C_8$-alkyl)-silyloxy, substituted or non-substituted tri($C_1$-$C_8$alkyl)-silyl, substituted or non-substituted $C_5$-$C_{12}$-fused bicycloalkyl, or substituted or non-substituted $C_5$-$C_{12}$-fused bicycloalkenyl;

or

Q represents a group of formula Z1;

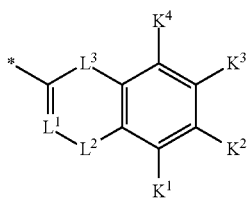

(Z¹)

and wherein $R^1$, $K^1$, $K^2$, $K^3$, $K^4$; $L^1$ $L^2$ and $L^3$ have the values described for (Z), or Q represents a group of formula $Z^2$;

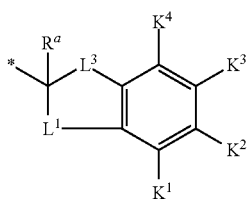

(Z²)

wherein $K^1$, $K^2$, $K^3$, $K^4$, $R^a$, $L^1$ and $L^3$ have the values described for (Z);

or

Q represents also a group of formula $Z^3$;

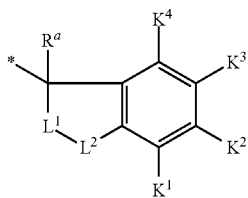

(Z³)

wherein $K^1$, $K^2$, $K^3$, $K^4$, $R^a$, $L^1$ and $L^2$ have the values described for (Z), unless indicated otherwise, a group or a substituent that is substituted according to the invention can be substituted by one or more of the following groups or atoms: a halogen atom, a nitro group, a hydroxy group, a cyano group, an isocyano group, an amino group, a sulphenyl group, a pentafluoro-☐⁶-sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a formylamino group, a (hydroxyimino)-$C_1$-$C_6$-alkyl group, a $C_1$-$C_8$-alkyl, a tri($C_1$-$C_8$-alkyl)silyl-$C_1$-$C_8$alkyl, $C_1$-$C_8$-cycloalkyl, tri($C_1$-$C_8$-alkyl)silyl-$C_1$-$C_8$cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$halogenoalkoxy having 1 to 5 halogen atoms, a $C_1$-$C_8$alkylsulphenyl, a $C_1$-$C_8$halogenoalkylsulphenyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$alkylcarbamoyl, a N—$C_1$-$C_8$-alkyloxycarbamoyl, a $C_1$-$C_8$alkoxycarbamoyl, a N—$C_1$-$C_8$-alkyl-$C_1$-$C_8$-alkoxycarbamoyl, a $C_1$-$C_8$alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, substituted or non-substituted $C_1$-$C_8$alkoxycarbonylamino, substituted or non-substituted $C_1$-$C_8$-halogenoalkoxycarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_8$-alkylaminosulfamoyl, a di-$C_1$-$C_6$alkylaminosulfamoyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, benzyloxy, benzylsulphenyl, benzylamino, phenoxy, phenylsulphenyl, or phenylamino;

as well as salts, N-oxides or (E) and (Z) isomers and mixtures thereof.

2. A compound according to claim 1, wherein X represents a hydrogen atom, a halogen atom, substituted or non-substituted $C_1$-$C_8$-alkyl, a substituted or non-substituted $C_1$-$C_8$-alkoxy, a cyano group, a methanesulfonyl group, a nitro group, a trifluoromethyl group or an aryl group.

3. A compound according to claim 1, wherein X represents a hydrogen atom.

4. A compound according to claim 1, wherein Y represents a substituted or non-substituted $C_1$-$C_8$-alkyl group.

5. A compound according to claim 1, wherein Y represents an alkyl group having 1 to 3 carbon atoms.

6. A compound according to claim 1, wherein R in the pyridyl group of formula (Het¹) represents a hydrogen atom or a halogen atom.

7. A compound according to claim 1, wherein R in the pyridyl group of formula (Het¹) represents a hydrogen atom or a chlorine atom.

8. A compound according to claim 1, wherein $R^a$ represents a hydrogen atom or a methyl group.

9. A compound according to claim 1, wherein n represents 1.

10. A compound according to claim 1, wherein $R^1$ and $R^2$ independently represent a hydrogen atom, a halogen atom, or substituted or non-substituted $C_1$-$C_8$-alkyl.

11. A compound according to claim 1, wherein $R^1$ and $R^2$ independently represent a hydrogen atom, a fluorine atom, or a methyl group.

12. A compound according to claim 1, wherein $K^1$, $K^2$, $K^3$ and $K^4$ independently represent a hydrogen atom, a halogen atom, a cyano group, substituted or non-substituted $C_1$-$C_8$- alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_3$-$C_8$-alkynyloxy, substituted or non-substituted ($C_1$-$C_6$-alkoxyimino)-$C_1$-$C_6$-alkyl, substituted or non-substituted phenoxy, substituted or non-substituted aryl, or substituted or non-substituted heterocyclyl.

13. A compound according to claim 1, wherein $K^1$, $K^2$, $K^3$ and $K^4$ independently represent a hydrogen atom, a halogen atom, a cyano group, substituted or non-substituted $C_1$-$C_8$-alkyl, substituted or non-substituted $C_1$-$C_8$-halogenoalkyl having 1 to 5 halogen atoms, substituted or non-substituted $C_1$-$C_8$-alkoxy.

14. A compound according to claim 1, wherein $K^1$, $K^2$, $K^3$ and $K^4$ independently represent a hydrogen atom, a halogen atom, a cyano group, $C_1$-$C_2$-alkyl, $C_1$-$C_2$-halogenoalkyl having 1 to 5 halogen atoms, $C_1$-$C_2$-alkoxy.

15. A fungicide composition comprising, as an active ingredient, an effective amount of a compound of formula (I) according to claim 1 and an agriculturally acceptable support, carrier or filler.

16. A method for controlling phytopathogenic fungi of crops, characterized in that an agronomically effective and substantially non-phytotoxic quantity of a compound according to claim 1 is applied to the soil where plants grow or are capable of growing, to the leaves and/or the fruit of plants or to the seeds of plants.

17. A method for controlling phytopathogenic fungi of crops, characterized in that an agronomically effective and substantially non-phytotoxic quantity of a composition according to claim 15 is applied to the soil where plants grow or are capable of growing, to the leaves and/or the fruit of plants or to the seeds of plants.

* * * * *